United States Patent [19]
Noyori et al.

[11] Patent Number: 5,532,402
[45] Date of Patent: Jul. 2, 1996

[54] PROCESS FOR PRODUCING OPTICALLY ACTIVE HYDROXYALKYLPHOSPHONATES

[75] Inventors: Ryoji Noyori, Aichi; Masato Kitamura, Nagoya; Makoto Tokunaga, Chiba, all of Japan

[73] Assignee: Takasago International Corporation, Tokyo, Japan

[21] Appl. No.: 402,654

[22] Filed: Mar. 13, 1995

[30] Foreign Application Priority Data

Jul. 1, 1994 [JP] Japan .................. 6-150837

[51] Int. Cl.$^6$ .................. C07F 9/40
[52] U.S. Cl. .................. 558/178
[58] Field of Search .................. 558/178

[56] References Cited

U.S. PATENT DOCUMENTS 3,883,580  5/1975  Solodar .................. 260/482 C

OTHER PUBLICATIONS

Kitamura et al. Tetrahedron Letters, vol. 32 No. 33, pp. 4163–4166 Month not available (1991).
Abstract of the 67th Spring Conference of the Chemical Society of Japan 4 E209: "Asymmetric Synthesis of Optically Active Hydroxyalkylphosphonates" Mar. 14, 1994.

*Primary Examiner*—Johann Richter
*Assistant Examiner*—Laura L. Stockton
*Attorney, Agent, or Firm*—Oblon, Spivak, McClelland, Maier & Neustadt

[57] ABSTRACT

Disclosed herein is a process for producing an optically active hydroxyalkylphosphonate represented by the formula (4), which comprises asymmetrically hydrogenating an oxoalkylphosphonate represented by the formula (1) using, as a catalyst, a ruthenium-optically active phosphine complex represented by the formula (2).

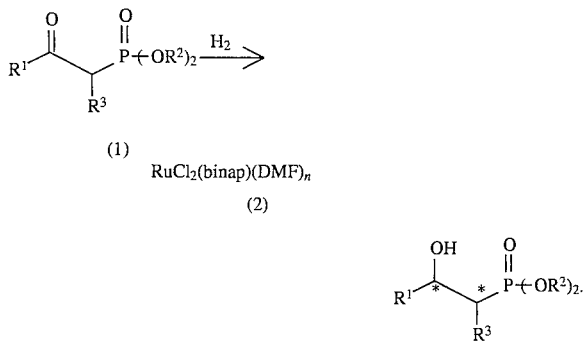

4 Claims, No Drawings

PROCESS FOR PRODUCING OPTICALLY ACTIVE HYDROXYALKYLPHOSPHONATES

BACKGROUND OF THE INVENTION

1. Field of the Invention

The present invention relates to a process for producing optically active hydroxyalkylphosphonates.

2. Description of the Background Art

Optically active hydroxyalkylphosphonates are compounds, which are useful as physiologically active substances, and moreover in recent years, have attracted much attention in the fields of bioorganic chemistry and medical chemistry as important intermediates for phosphonic analogues of amino acid-based peptides, haptens in catalytic antibody chemistry, etc., and as important intermediates for fosfomycin which is one of practical antibiotics.

The optically active hydroxyalkylphosphonates have heretofore been obtained by optical resolution. For example, Japanese Patent Publication No. 19264/1974 has proposed a process in which 1-propenylphosphonic acid is converted to its halohydrin with hypohalogen acid, and the halohydrin is then optically resolved by an optically resolving agent using optically active α-phenetylamine to obtain a (+)-threo-(1-halo-2-hydroxypropyl)phosphonic acid derivative.

Besides, Japanese Patent Application Laid-Open No. 22593/1988 has proposed a process in which 1-propenylphosphonic acid is esterified with tartaric acid and then converted to its halohydrin, and the halohydrin is optically resolved, thereby obtaining an optically active 1-halo-2-hydroxypropylphosphonic acid.

As described above, the conventional processes for producing the optically active hydroxyalkylphosphonates have used an expensive, optically resolving agent or required a multi-step reaction process. There has thus been a demand for development of a process capable of more simply and cheaply producing optically active hydroxyalkylphosphonates having a high optical purity.

SUMMARY OF THE INVENTION

With the foregoing circumstances in view, the present inventors have carried out an extensive investigation. As a result, it has been found that when an oxoalkylphosphonate, which is a specific compound, is subjected to an asymmetric hydrogenation reaction using a ruthenium-optically active phosphine complex as a catalyst, an optically active hydroxyalkylphosphonate having a high optical purity can be obtained, thus leading to completion of the present invention.

In an aspect of the present invention, there is thus provided a process for producing an optically active hydroxyalkylphosphonate represented by the following general formula (4):

$$R^1 \underset{R^3}{\overset{OH}{\underset{*}{\bigwedge}}} \overset{*}{\underset{}{}} P(OR^2)_2 \quad (4)$$

wherein $R^1$ and $R^2$ are identical with or different from each other and mean individually an alkyl group, $R^3$ denotes a halogen atom, and * stands for an asymmetric carbon atom, which comprises asymmetrically hydrogenating an oxoalkylphosphonate represented by the following general formula (1):

$$R^1 \underset{R^3}{\overset{O}{\underset{}{\bigwedge}}} \overset{O}{\underset{}{}} P(R^2)_2 \quad (1)$$

wherein $R^1$, $R^2$ and $R^3$ have the same meaning as defined above, using, as a catalyst, a ruthenium-optically active phosphine complex represented by the following general formula (2):

$$RuCl_2(binap)(DMF)_n \quad (2)$$

wherein binap means an optically active bisphosphine represented by the following general formula (3):

$$\text{(binap structure with } R^4, R^5, R^6, R^7 \text{)} \quad (3)$$

in which $R^4$, $R^5$, $R^6$ and $R^7$ are identical with or different from one another and denote individually a phenyl group which may be substituted by an alkyl or alkoxy, DMF means N,N-dimethylformamide, and n stands for a natural number.

According to the present invention, (1R,2S)-1-halogeno-2-hydroxypropylphosphonates, which are important intermediates for fosfomycin, can be simply produced with high yield and optical purity.

The above and other objects, features and advantages of the present invention will become apparent from the following description and the appended claims.

DETAILED DESCRIPTION OF THE INVENTION AND PREFERRED EMBODIMENTS

The process according to the present invention is expressed by the following reaction scheme:

$$R^1 \underset{R^3}{\overset{O}{\underset{}{\bigwedge}}} \overset{O}{\underset{}{}} P(OR^2)_2 \xrightarrow{H_2}$$

(1)

$$RuCl_2(binap)(DMF)_n$$

(2)

$$R^1 \underset{R^3}{\overset{OH}{\underset{*}{\bigwedge}}} \overset{*}{\underset{}{}} \overset{O}{\underset{}{}} P(OR^2)_2$$

wherein $R^1$, $R^2$, $R^3$, *, binap DMF and n have the same meaning as defined above, respectively.

In the general formula (1), no particular limitation is imposed on the alkyl groups represented by $R^1$ and $R^2$. However, they may preferably be alkyl groups having 1–6 carbon atoms, with alkyl groups having 1–4 carbon atoms being more preferred. Specific examples thereof include methyl, ethyl, n-propyl, isopropyl, n-butyl, isobutyl, sec-butyl and tert-butyl groups. However, it is particularly preferred that both $R^1$ and $R^2$ be methyl groups. Besides, examples of the halogen atom include chlorine, bromine, iodine and fluorine atoms. Of these examples, bromine atom is particularly preferred.

Preferable specific examples of the oxoalkylphosphonate represented by the general formula (1) include dimethyl 1-bromo-2-oxopropylphosphonate, diethyl 1-bromo-2-oxopropylphosphonate, di(n-propyl) 1-bromo-2-oxopropylphosphonate, dimethyl 1-bromo-2-oxobutylphosphonate, dimethyl 1-bromo-2-oxopentylphosphonate, dimethyl 1-bromo-2-oxohexylphosphonate and dimethyl 1-chloro-2-oxopropylphosphonate.

These oxoalkylphosphonates can be synthesized with ease, for example, by the Arbusow reaction of an α-haloketone and a trialkylphosphite [Pure Appl. Chem., 9, 307 (1964)]. They can also be synthesized by a process in which after a dialkyl methanephosphonate is converted to a carbo anion with a base such as n-butyllithium, this product is reacted with a lower carboxylic acid ester or a lower aldehyde, followed by an oxidation reaction [Synthesis, 691 (1984)].

The ruthenium-optically active phosphine complex used as the asymmetric hydrogenation catalyst in the present invention is represented by the general formula (2). No particular limitation is imposed on the alkyl groups which are substituents on the phenyl groups represented by $R^4$, $R^5$, $R^6$ and $R^7$ in the general formula (3) which means a ligand of this complex. However, they may preferably be alkyl groups having 1–6 carbon atoms, with alkyl groups having 1–4 carbon atoms being more preferred. Specific examples thereof include methyl, ethyl, n-propyl, isopropyl, n-butyl, isobutyl, sec-butyl and tert-butyl groups. No particular limitation is also imposed on the alkoxy groups as the substituents on the phenyl groups. However, they may preferably be alkoxy groups having 1–6 carbon atoms, with alkoxy groups having 1–4 carbon atoms being more preferred. A methoxy group is most preferred. Preferable examples of $R^4$, $R^5$, $R^6$ and $R^7$ include methylphenyl, methoxyphenyl and phenyl group. Of these examples, phenyl group is particularly preferred.

The ruthenium-phosphine complex used as a catalyst in the present invention can be obtained in accordance with, for example, the following process. Namely, as described in "Tetrahedron Lett. 32, 4163–4166 (1991)", an optically active phosphine represented by the general formula (3) is added to a ruthenium complex such as [$RuCl_2$ (benzene)]$_2$ to heat them in DMF as a solvent to about 100° C. Thereafter, the reaction mixture is cooled down and concentrated under reduced pressure, thereby obtaining this complex.

Specific examples of the ruthenium-optically active phosphine complex (2) include $RuCl_2$ (Ph-binap) $(DMF)_n$ [hereinafter, Ph-binap means 2,2'-bis(diphenylphosphino) 1,1'-binaphtyl], $RuCl_2$ (T-binap)$(DMF)_n$ [hereinafter, T-binap means 2,2'-bis(di(p-tolyl)phosphino)-1,1'-binaphtyl], $RuCl_2$ (mT-binap)$(DMF)_n$ [hereinafter, mT-binap means 2,2'-bis (di(m-tolyl)phosphino)-1,1'-binaphtyl], $RuCl_2$ (MO-binap) $(DMF)_n$ [hereinafter, MO-binap means 2,2'-bis (di(p-methoxyphenyl)phosphino)-1,1'-binaphtyl], and $RuCl_2$ (Xy-binap)$(DMF)_n$ [hereinafter, Xy-binap means 2,2'-bis (di(3, 5-xylyl)phosphino)-1,1'-binaphtyl].

Incidentally, all the bisphosphines in the above complexes include both types; (R) isomer and (S) isomer of absolute configuration. Note that such symbolic marks are hereinafter omitted.

In the practice of the present invention, it is only necessary to add the ruthenium-optically active phosphine complex (2), the oxoalkylphosphonate (1) and a solvent to an autoclave in an atmosphere of inert gas such as nitrogen or argon and conduct asymmetric hydrogenation in a hydrogen atmosphere.

The amount of the ruthenium-optically active phosphine complex (2) used as a catalyst is preferably within a range of from 1/1000 to 1/100 tool, particularly preferably from 1/500 to 1/100 tool per tool of the oxoalkylphosphonate (1) as a starting compound.

Any solvent may be used so far as it is a solvent generally used in asymmetric hydrogenation. However, alcohols such as methanol and ethanol, and methylene chloride are preferred, with methanol being particularly preferred.

The temperature and reaction time upon the asymmetric hydrogenation may vary depending on the kind of catalyst and other conditions. However, the asymmetric hydrogenation may generally be conducted at a temperature of 10–100° C., preferably 20–60° C. for about 15–100 hours, preferably 20–88 hours. Besides, the hydrogen pressure may be preset to about 1–150 kg/cm$^2$, preferably 3–100 kg/cm$^2$.

After completion of the reaction, the solvent may be removed to purify the reaction product, thereby obtaining the optically active hydroxyalkylphosphonate represented by the general formula (4).

Examples of the optically active hydroxyalkylphosphonate obtained by the process of the present invention include dimethyl 1-bromo-2-hydroxy-propylphosphonate, dimethyl 1-bromo-2-hydroxybutylphosphonate, dimethyl 1-bromo-2-hydroxypentylphosphonate, dimethyl 1-bromo -2-hydroxyhexylphosphonate, dimethyl 1-chloro-2hydroxypropylphosphonate, diethyl 1-bromo-2-hydroxypropylphosphonate, di(n-propyl) 1-bromo-2-hydroxypropylphosphonate and di(n-butyl) 1-bromo-2-hydroxypropylphosphonate.

In order to produce fosfomycin using any one of the (1R,2S)-1-bromo-2-hydroxypropylphosphonates obtained in the present invention, such an ester is hydrolyzed at its ester moiety with hydrogen bromide or the like into (1R, 2S)-1-bromo-2-hydroxypropylphosphonic acid, followed by its epoxidation, thereby obtaining fosfomycin. The thus-obtained fosfomycin may be converted to a salt of a metal such as sodium or calcium. More specifically, disodium fosfomycin, calcium fosfomycin monohydrate or the like may be obtained.

The present invention will hereinafter be described in detail by reference to examples. However, it should be borne in mind that this invention is not limited to and by these examples. Incidentally, the analytical data in each example were measured by means of the following instruments:

Nuclear magnetic resonance spectrum ($^1$H-NMR):
  JNM-GX270 (manufactured by JEOL, Ltd.).
Liquid chromatography (HPLC):
  LC-6A (manufactured by Shimadzu Corporation),
  Injector: RHEODYEN 7125,
  UV detector: SPD-6A (manufactured by Shimadzu Corporation).

Example 1

[Synthesis of dimethyl (1R,2S)-1-bromo-2-hydroxypropylphosphonate]

(1) Synthesis of dimethyl 2-oxopropylphosphonate:

A 2-liter eggplant type flask was charged with 179.2 g (1.081 mol) of potassium iodide, 300 ml of acetone and 250 ml of acetonitrile, to which 100 g (1.081 mol) of chloroacetone were added, thereby forming a white suspension. Further, 134 g (1,081 tool) of trimethylphosphite were added to stir the resulting mixture for 6 hours at 20° C. and for 4 hours at 50° C. After the thus-obtained solution was filtered through Celite, the solvent was distilled off to obtain a product in the form of a brown oil. This oily product was subjected to fractional distillation under reduced pressure (at 81–85° C. and 0.02 mmHg) to obtain 127.5 g (yield: 71%) of dimethyl 2-oxopropylphosphonate. The result of analysis of this compound by $^1$H-NMP is described below.

$^1$H-NMR (270 MHz, CDCl$_3$) δ:

2.30(s,3,CH$_3$), 3.08(d,2,J=11 Hz,OCH$_3$), 3.77(d,6,J=11 Hz,OCH$_3$).

(2) Synthesis of dimethyl 1-bromo-2-oxopropylphosphonate:

A 1-liter eggplant type flask was charged with 30.1 g (0.181 mol) of dimethyl 2-oxopropylphosphonate and 300 ml of tetrahydrofuran, to which 18.5 ml (0.181 mol) of 30% aqueous hydrogen peroxide and 20.3 ml (0.181 mol) of a 49% aqueous solution of hydrobromic acid were added over 3 hours at 20° C. using a dropping funnel. Thereafter, the contents were stirred for 3 hours at 20° C. To the resultant mixture, 200 ml of water and 100 ml of diethyl ether (hereinafter referred to as "ether") were added to vigorously stir the resulting liquid mixture, followed by separation of liquids. After sodium chloride was added to the resultant water layer to saturation, the saturated solution was subjected to extraction twice with ether and once with ethyl acetate. The thus-obtained organic layers were collected, dried over sodium sulfate and then filtered. The solvent was distilled out of the resulting filtrate, thereby obtaining 31.8 g of a product in the form of a yellow oil.

This oily product was dissolved in 100 ml of ether, and the resulting solution was subjected to extraction 5 times with 80 ml of water. After the water layers were collected and washed with 100 ml of ether, sodium chloride was added to the collected water layer to saturation. This water layer was subjected to extraction 5 times with 100 ml of ether, thereby obtaining 25.6 g of a product in the form of a yellow oil. This oily product was subsequently distilled under reduced pressure (at 90–100° C. and 0.01 mmHg) to obtain 23.0 g (yield: 52%) of dimethyl 1-bromo-2-oxopropylphosphonate. The result of analysis of this compound by $^1$H-NMP is described below.

$^1$H-NMR (270 MHz, CDCl$_3$)δ:

2-48(s,CH$_3$), 3-88(d,J=11 Hz,OCH$_3$), 3-89(d,6,J=11 Hz,OCH$_3$), 4.40(d,1,J=15 Hz,CHBr).

(3) Synthesis of RuCl$_2$((S)-Ph-binap) (DMF)$_n$:

A 20-ml Schlenk's tube was charged with 43.5 mg (87.3 μmol) of [RuCl$_2$(benzene)]$_2$, 113.7 mg (0.183 mmol) of (S)-Ph-binap and 3.0 ml of N,N-dimethylformamide, and the resulting mixture was stirred for 10 minutes at 100° C. in an argon atmosphere. After the stirring, the resulting reddish brown reaction mixture was cooled, stirred for 1 hour under 0.1 mmHg and concentrated at 50° C. under 0.1 mmHg, thereby quantitatively obtaining RuCl$_2$((S)-Ph-binap) (DMF)$_n$ as a reddish brown solid.

(4) Synthesis of dimethyl (1R,2S)-1-bromo-2-hydroxypropylphosphonate:

A 20-ml Schlenk's tube which had been dried under reduced pressure and purged with argon in advance was charged with 1.65 g (6.73 mmol) of dimethyl 1-bromo-2-oxopropylphosphonate and 20 ml of methanol to conduct freeze deaeration 3 times. To the resulting mixture, 11.0 mg (13.8 μmol) of RuCl$_2$((S)-Ph-binap)(DMF)$_n$ were added in an argon stream. The resulting solution of a yellowish red color was subjected to freeze deaeration further twice. This solution was dried under reduced pressure and transferred to a 400-ml glass autoclave equipped with a glass tube and purged with argon through a stainless steel tube making good use of an argon pressure. A hydrogen cylinder was connected to the autoclave through an hydrogen inlet tube to purge the interior of the autoclave 10 times with hydrogen under a pressure of 3 atm. Thereafter, the autoclave was kept under a hydrogen pressure of 3 atm to stir the solution for 85 hours at 25° C. After completion of the reaction, the resulting solution of a yellowish red color was concentrated under reduced pressure to obtain a 85:15 mixture of dimethyl 1-bromo-2-hydroxypropylphosphonate and dimethyl 2-hydroxypropylphosphonate A ratio of the syn isomer to the anti isomer in dimethyl 1-bromo-2-hydroxypropylphosphonate was 91:9.

The enantiomer excess (e.e.%) of the syn isomer was determined by converting the product to its (S)-naphthylethyl carbamate derivative by the following procedure and subjecting the derivative to reversed phase HPLC. More specifically, a glass tube of 8 mm long, one end of which had been sealed, was charged with 15 mg (0.061 mmol) of dimethyl 1-bromo-2-hydroxypropylphosphonate, 15 mg (0.061 mmol) of (S)-naphthylethyl isocyanate and 1 ml of toluene. The other end of the tube was also sealed under reduced pressure, and the contents were heated for 40 hours at 120° C. After cooling, one end of the tube was opened to distill off the solvent, thereby obtaining a crude product. This crude product was purified through a silica gel column (silica gel: Fuji-Davison BW300, 2 g; hexane/ethyl acetate =1/3, ethanol/dichloromethane =1/30) to obtain the (S)-naphthylethyl carbamate derivative. The thus-obtained (S)-naphthylethyl carbamate derivative was analyzed by reversed phase HPLC (column: Develosil ODS-5; solvent: water/acetonitrile =3/2; flow rate: 1 ml/min; detection light: UV 254 nm). As a result, retention time was found to be; 24.8 minutes (1R,2S), 27.7 minutes (1S,2R), 33.2 minutes (1S,2S) and 35.3 minutes (1R,2R).

From this analytical result, the enantiomer excess of the syn isomer (1R,2S) was found to be 96 e.e.%. The result of analysis of the thus-obtained compound by $^1$H-NMP is described below.

$^1$H-NMR (270 MHz, CDCl$_3$) δ:

1.42(d,3,J=6 Hz,CH$_3$), 3.83(d,3,J=10 Hz,OCH$_3$), 3.88(d,3,J=10 Hz,OCH$_3$), 3.88(dd,1,J=10 Hz,CHBr), 4.15 (m,1,CHOH).

Example 2

The same procedure as in Example 1 was followed except that the amount of RuCl$_2$((S)-Ph-binap)(DMF)$_n$ in Example 1 (4) was changed 29.8 mg, thereby obtaining dimethyl 1-bromo-2-hydroxypropylphosphonate containing the syn isomer and the anti isomer at a ratio of 73/27, said syn isomer (1R,2S) having an enantiomer excess higher than 90e.e.%.

Referential Example 1

[Synthesis of (1R,2S)-1-bromo-2-hydroxypropylphosphonic acid]

Following the method of Giordano, C, et al. [J. Org. Chem., 54, 1470(1989)], 100 mg of dimethyl (1R,2S)-1-bromo-2-hydroxypropylphosphonate were added to 1 ml of a 49% aqueous solution of hydrobromic acid, and the resulting mixture was stirred for 14 hours at 95° C. The solvent was distilled out of the reaction mixture to obtain (1R,2S)-1-bromo-2-hydroxypropylphosphonic acid in the form of a colorless oil. The result of analysis of the thus-obtained compound by $^1$H-NMP is described below.

$^1$H-NMR (270 MHz, D$_2$O) δ:

1.34(dd,3,J=6 Hz,1 Hz,CH$_3$), 3.98(dd,1,J=12 Hz,4 Hz,OCH$_3$), 4.20(ddq,1,J=9 Hz,6 Hz,4 Hz, CHBr).

What is claimed is:

1. A process for producing an optically active hydroxyalkylphosphonate represented by the following general formula (4):

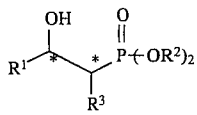

wherein $R^1$ and $R^2$ are identical with or different from each other and mean individually an alkyl group, $R^3$ denotes a halogen atom, and * stands for an asymmetric carbon atom, which comprises asymmetrically hydrogenating an oxoalkylphosphonate having an asymmetric carbon atom as represented by the following general formula (1):

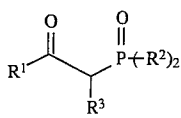

wherein $R^1$, $R^2$ and $R^3$ have the same meaning as defined above, using, as a catalyst, a ruthenium-optically active phosphine complex represented by the following general formula (2):

$$RuCl_2(binap)(DMF)_n \qquad (2)$$

wherein binap means an optically active bisphosphine represented by the following general formula (3):

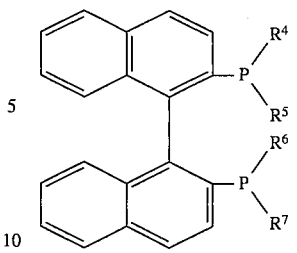

in which $R^4$, $R^5$, $R^6$ and $R^7$ are identical with or different from one another and denote individually a phenyl group which may be substituted by an alkyl or alkoxy, DMF means N,N-dimethylformamide, and n stands for a natural number.

2. The process according to claim 1, wherein in the compound represented by the general formula (1), $R^1$ and $R^2$ are individually an alkyl group having 1–6 carbon atoms, and in the optically active bisphosphine represented by the general formula (3), $R^4$, $R^5$, $R^6$ and $R^7$ are individually a phenyl group which may be substituted by an alkyl having 1–6 carbon atoms or methoxy.

3. The process according to claim 1, wherein in the compound represented by the general formula (1), $R^1$ and $R^2$ are individually a methyl group, and $R^3$ is a bromine atom, and in the optically active bisphosphine represented by the general formula (3), $R^4$, $R^5$, $R^6$ and $R^7$ are individually a phenyl group.

4. The process according to claim 1, wherein the optically active hydroxyalkylphosphonate is dimethyl (1R,2S)-1-bromo-2-hydroxypropylphosphonate.

* * * * *

UNITED STATES PATENT AND TRADEMARK OFFICE
CERTIFICATE OF CORRECTION

PATENT NO. : 5,532,402

DATED : July 2, 1996

INVENTOR(S) : Ryoji NOYORI, et al.

It is certified that error appears in the above-identified patent and that said Letters Patent is hereby corrected as shown below:

col. 2, line 58, "binap DMF" should read --binap, DMF--.

Column 3, line 14, underline "9".
        line 43, underline "32".
        line 51, "(diphenylphosphino)" should read
--(diphenylphosphino)- --.

Column 4, line 5, "1/100 tool" should read --1/100 mol--.
        line 6, "1/100 tool per tool" should read
--1/100 mol per mol--.
        line 28, "1-chloro-2hydroxypropylphos-" should read
--1-chloro-2-hydroxypropylphos- --.
        line 65, "134g (1,081 tool)" should read
--134g (1.081 mol)--.

Column 5, line 41, "2-48(s,CH$_3$),3-88" should read
--2.48(s,CH$_3$),3.88--
        line 42, "3-89" should read --3.89--.

UNITED STATES PATENT AND TRADEMARK OFFICE
CERTIFICATE OF CORRECTION

PATENT NO.   : 5,532,402
DATED        : July 2, 1996
INVENTOR(S)  : Ryoji NOYORI, et al It is certified that error appears in the above-identified patent and that said Letters Patent is hereby corrected as shown below:

Column 6, line 9, Insert a period (.) After
     "droxypropylphosphonate".
          line 31, Delete semicolon (;) after "be".
          line 56, Underline "54".

Signed and Sealed this

Fourteenth Day of April, 1998

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,532,402
DATED : July 2, 1996
INVENTOR(S) : Ryoji Noyori, et al.

It is certified that error appears in the above-identified patent and that said Letters Patent is hereby corrected as shown below:

Column 2, lines 1 thru 5, Formula

"

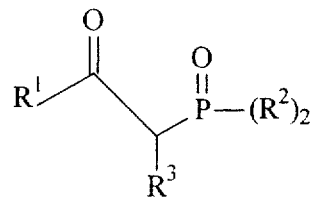

"

should read

--

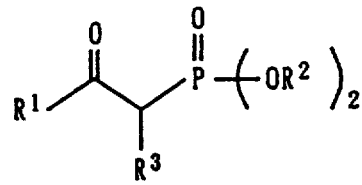

--.

UNITED STATES PATENT AND TRADEMARK OFFICE
CERTIFICATE OF CORRECTION

PATENT NO. : 5,532,402
DATED : July 2, 1996
INVENTOR(S) : Ryoji Noyori, et al.

It is certified that error appears in the above-identified patent and that said Letters Patent is hereby corrected as shown below:

Column 7, line 18-23, Formula

"
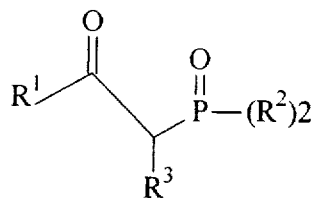
"

UNITED STATES PATENT AND TRADEMARK OFFICE
CERTIFICATE OF CORRECTION

PATENT NO. : 5,532,402
DATED : July 2, 1996
INVENTOR(S) : Ryoji Noyori, et al.

It is certified that error appears in the above-identified patent and that said Letters Patent is hereby corrected as shown below:

should read

--

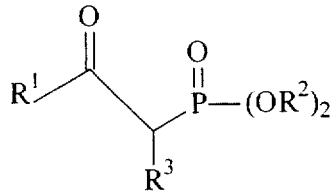

--.

Signed and Sealed this

Fifteenth Day of September, 1998

*Attest:*

BRUCE LEHMAN

*Attesting Officer*         *Commissioner of Patents and Trademarks*